(12) United States Patent
Karavias (10) Patent No.: US 10,993,549 B2
(45) Date of Patent: *May 4, 2021

(54) DIAPER CHANGING APPARATUS (71) Applicant: Aaron James Karavias, Portsmouth, VA (US)

(72) Inventor: Aaron James Karavias, Portsmouth, VA (US)

( * ) Notice: Subject to any disclaimer, the term of this patent is extended or adjusted under 35 U.S.C. 154(b) by 317 days.

This patent is subject to a terminal disclaimer.

(21) Appl. No.: 16/030,698

(22) Filed: Jul. 9, 2018

(65) Prior Publication Data

US 2018/0310722 A1 Nov. 1, 2018

Related U.S. Application Data (63) Continuation of application No. 14/706,877, filed on May 7, 2015, now Pat. No. 10,058,193.

(51) Int. Cl.
| | |
|---|---|
| *A47D 5/00* | (2006.01) |
| *A61F 5/37* | (2006.01) |
| *A47D 15/00* | (2006.01) |
| *A61G 7/10* | (2006.01) |
| *A61F 13/84* | (2006.01) |

(52) U.S. Cl.
CPC ............ *A47D 5/00* (2013.01); *A47D 15/005* (2013.01); *A61F 5/37* (2013.01); *A61F 5/3761* (2013.01); *A61F 5/3769* (2013.01); *A61F 13/84* (2013.01); *A61G 7/1009* (2013.01)

(58) Field of Classification Search
CPC ...... A61G 7/047; A61G 7/075; A61G 7/0755; A61G 7/1009; A61G 13/0009; A61G 13/123; A61G 13/124; A61G 13/125; A47D 5/00; A61F 5/37; A61F 5/3761; A61F 5/3769
USPC ................ 128/845, 846, 869, 870, 873–876; 5/648–650, 655
See application file for complete search history.

(56) References Cited

U.S. PATENT DOCUMENTS

| | | |
|---|---|---|
| 3,817,512 A | 6/1974 | Torrey |
| 5,337,427 A | 8/1994 | Pagano et al. |
| 5,799,654 A | 9/1998 | Kassan |
| 6,698,044 B2 | 3/2004 | Greenfield et al. |
| 6,755,198 B2 | 6/2004 | Parker |
| 6,854,142 B2 | 2/2005 | Lukomskiy |
| 7,065,814 B2 | 6/2006 | Rutkowski |
| 7,536,734 B2 | 5/2009 | Heimbrock |

(Continued)

*Primary Examiner* — Keri J Nelson
(74) *Attorney, Agent, or Firm* — Winston & Strawn LLP (57) ABSTRACT A diaper changing apparatus that restrains an infant, child, or special need individual in a way that aids the caregiver's ability to manipulate his or her position and orientation to provide access to the diaper area during diaper changing activities. The apparatus allows the caregiver to easily lift the legs and buttocks, providing access to the underside of the infant, child, or special need individual for diaper changing activities. In some embodiments, adjustments to the height of the legs and buttocks and the separation of the legs may be made during a diaper change by moving a restraint of the apparatus in the direction of the desired adjustment. Some embodiments aid a caregiver by restraining the arms, chest, or torso to prevent the infant, child, or special needs individual from interfering with the diaper change, but without immobilizing him so much that the caregiver cannot easily adjust his position.

21 Claims, 9 Drawing Sheets (56) References Cited

U.S. PATENT DOCUMENTS

| | | |
|---|---|---|
| 10,058,193 B2 * | 8/2018 | Karavias .................. A61F 5/37 |
| 2005/0235424 A1 | 10/2005 | Waite |
| 2011/0209716 A1 | 9/2011 | Scarsbrook |
| 2014/0359946 A1 | 12/2014 | Kong |
| 2015/0327689 A1 | 11/2015 | Howard |

* cited by examiner

DIAPER CHANGING APPARATUS

CROSS-REFERENCE TO RELATED APPLICATIONS

This application claims the benefit of U.S. application Ser. No. 14/706,877, filed May 7, 2015, the entirety of which is herein incorporated by reference.

BACKGROUND OF THE INVENTION

When changing the diaper of an infant, toddler, or special needs individual, a caregiver must traditionally hold and lift the legs with one hand and clean the diaper area with the other hand. In this patent, "person" refers to infants, toddlers, or special needs individuals in need of a diaper change. The task of changing the person's diaper is challenging because of the person's tendency to roll over or squirm out of the caregiver's grasp. Moreover, using a single hand for diapering activities as in the traditional method is especially challenging because of the person's tendency to soil himself and the caregiver during the diaper change. With the traditional method, it is not possible to simultaneously (1) separate the person's legs to clean the groin area; (2) lift the person's legs and buttocks to clean the buttocks; (3) restrain the person from rolling over or from interfering with the diaper change; and (4) containing waste generated during the diaper change. The prior art fails to address these problems.

U.S. Pat. No. 5,799,654 (the "'654 patent") discloses a set of ankle restraints and a handle for lifting the restrained ankles upward. Because the invention disclosed in the '654 patent requires the caregiver to hold and lift the handle upward, the patented invention fails to solve the problem of freeing up both hands for diapering activities. The infant's buttocks are lifted only while the caregiver lifts the handle of the device. There is no way to lock the height of the infant in place so one hand must always be holding and lifting the handle during diapering activities. Moreover, the invention described in the '654 patent does not allow for separating the infant's legs or adjusting the distance between the infant's legs during the diaper change. The legs are separated at all times by a fixed, "slightly separated" width. The claims and specification reveal there is no way to adjust the separation of the legs either to fit the device to infants of different sizes or to properly clean soiled areas in the groin region. The '654 patent provides no mechanism for restraining the infant's hands to prevent him or her from interfering with the diaper change and no mechanism for preventing the child from rolling over. The '654 patent also never mentions methods for containing waste generated during the diaper change.

U.S. Pat. No. 6,854,142 (the "'142 patent") discloses a diaper changing table that includes two rods with stirrups and a foot pedal that raises the rods. The lifting force in this invention comes from below as the rods are pushed upward. Although this invention allows for a hands-free operation of lifting the infant's legs and buttocks, there is no ability to adjust the separation of the legs. Further, the invention described in the '142 patent fails to allow the caregiver to adjust the height of the infant's buttocks easily during a diaper change. Instead, the specification and claims make clear that there are only two different heights allowed by the device during a diaper change ("a first and second position"). Adjusting the device to achieve any other heights involves significant effort because "if the stirrup needs to be a little higher or a little lower, the setscrew can be loosened, the rods can be adjusted in length and the setscrew could be tightened again to fasten the rods back together." Not being able to easily adjust the device to raise the infant's buttocks to many different heights during a diaper change negatively impacts the utility of the device. The invention described by the '142 patent is also a "piece of furniture" and is therefore not easily moved to different locations and is not easily used on different surfaces. The invention described by the '142 patent also requires that the caregiver continually depress the pedal to keep the infant's legs raised. The '142 patent provides no mechanism for restraining the infant's hands to prevent him or her from interfering with the diaper change and no mechanism for preventing the child from rolling over. There is also no mechanism for catching the infant's waste produced during the diaper change.

U.S. Publication No. 2005/0235424 (the "'424 publication") is comprised of a bed that tapers off near the child's buttocks to allow the child's buttock's to hang over the end of the device. This device does not easily facilitate access to the child's buttocks because the amount of space the operator has to clean the buttocks is limited by the fixed distance between the basin of the device and the child's buttocks. If the device is placed so that the child is close to horizontal (which is an ideal position to set the child down in) little room is available between the surface on which the device lies and the buttocks, making it difficult to clean the diaper area. In addition, the device includes a pair of stirrups for restraining the legs of the child, but these stirrups are only adjustable via a telescope adjustor. The telescope adjustor does not allow for adjusting the distance between the infant's legs; it only allows for adjusting the length of the stirrups. The '424 publication provides no mechanism for restraining the child's hands to prevent him or her from interfering with the diaper change. Although the '424 publication provides a chest strap, the chest strap is attached to a rigid base. The rigid base impedes a caregiver's ability to lift, turn, and move the child's legs, buttocks, and torso for improved access to the diaper area. The '424 publication also never discusses a mechanism for catching the child's waste produced during the diaper change.

U.S. Pat. No. 6,755,198 (the '198 patent") is directed to a system for restraining the upper torso of a child or infant for diapering activities. The system provides a rigid base on which the child is laid and a pair of chest straps arranged in a crisscrossing manner. This device does not allow a caregiver to simultaneously lift and separate the legs of a baby to provide access to the diaper area during a diaper change and it does not leave both of the caregiver's hands free to engage in diaper changing activities. The '198 patent provides no mechanism for restraining the child's hands to prevent him or her from interfering with the diaper change. Although the '198 patent provides a crisscrossed chest strap, the crisscrossed chest strap is attached to a rigid base. The rigid base impedes a caregiver's attempt to lift, turn, and move the child's legs, buttocks, and torso for improved access to the diaper area. The invention described by the '198 patent also fails to include a way to fix the position of the infant's buttocks and legs into place and never discusses a mechanism for catching the child's waste produced during the diaper change.

In summary, the prior art does not adequately provide a solution to the need for an apparatus to lift the legs and buttocks and separate the legs of the person in need of a diaper change, the need for an apparatus that can be adjusted easily during a diaper change to many different positions, the need for an apparatus that frees both of the caregiver's hands to help clean the soiled person, the need for an apparatus that restrains a person's hands to prevent him or her from interfering with diaper changing activities, the need for an apparatus to prevent the person from squirming or rolling over while still allowing enough flexibility to allow the caregiver to lift and turn the legs, torso, and buttocks of the person, the need for the caregiver to fix the position of the person's legs and buttocks in place, or the need for an apparatus that catches waste or urine produced during the diaper change. There is a continuing need for a new diaper changing device to meet these objectives.

SUMMARY OF THE INVENTION

The present invention provides a diaper changing apparatus that restrains the person in a way that aids the caregiver's ability to manipulate the position and orientation of the person's legs and buttocks. Some embodiments provide an adjustable diaper changing apparatus that allows a caregiver to lift and separate the legs of a person to provide access to the diaper area during a diaper change with minimal hand involvement. Some embodiments of the invention include a set of arms that attach to the person's legs or feet through restraints. The caregiver may move the arms during a diaper change, which in turn raises or lowers the buttocks of the person. The apparatus also allows the caregiver to easily adjust the distance between the person's legs during a diaper change.

In some embodiments of the invention, the height of the person's buttocks and the separation of the person's legs may be adjusted easily during the diaper change. Adjustments to the height of the buttocks and the separation of the legs may be made during a diaper change by simply moving an arm of the adjustable diaper changing apparatus in the direction of the desired adjustment. Some embodiments of the apparatus allow the caregiver to lock the person's legs and buttocks in the desired position so the caregiver may use both hands to clean and diaper the person. Some embodiments of the present invention include absorbent pads whose position may be adjusted to catch waste or urine produced during the diaper change.

Some embodiments of the diaper changing apparatus aid a caregiver in diapering activities by restraining the person's arms and/or chest or torso to prevent the person from interfering with the diaper change, but without immobilizing the person so much that the caregiver cannot easily lift the person's legs and buttocks or adjust the position of the person for improved access to the diaper area. In some of these embodiments, arm restraints allow the person to have some movement so that the person can remain comfortable while he or she is moved through a variety of positions during the diaper change. Also, in these embodiments, the person is lying on a semi-rigid pad that is capable of bending upwards and downwards as the caregiver lifts the person's legs and buttocks during the diaper change. The semi-rigid pad, however, has limited capability of twisting side-to-side so as to secure the person's torso and to prevent the person from rolling over during the diaper change. A chest or torso restraint is attached to the semi-rigid pad to secure the person.

These and other features of the present invention will become more apparent upon consideration of the detailed description and accompanying drawings.

BRIEF DESCRIPTION OF THE DRAWINGS

Preferred and non-limiting features of the invention will now be described in connection with the appended drawing figures, wherein.

DETAIL DESCRIPTION OF THE PREFERRED EMBODIMENTS

Figure 1:
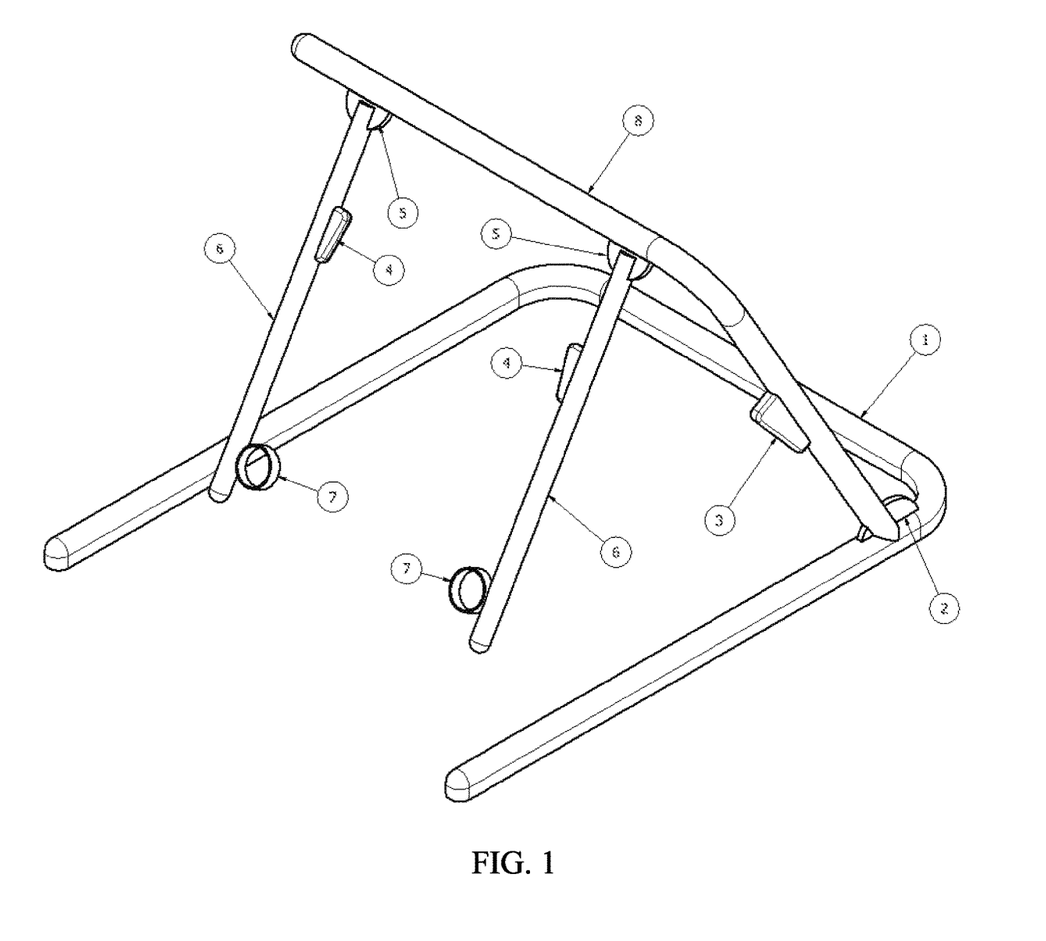
FIG. 1 is a perspective view of one embodiment of the invention.

One embodiment of the present invention is illustrated in FIG. 1. The device includes a base (1) to provide support for the device. The base in FIG. 1 is tubular, but the base may be a variety of different shapes as long as it performs the function of supporting the device or being a structure that other elements of the device can connect to. The base (1) may be placed on and/or fastened to a surface through any fastening method (e.g. screws, adhesive, hook and loop, etc.). There are a variety of surfaces to which the apparatus may be fastened, including a floor, wall, furniture such as a table or a crib, etc. The base (1) is connected to the main adjustable connection (2), which also connects to a primary arm (8). There can be more than one primary arm (8).

The secondary arms (6) are attached to the primary arm (8) via a secondary adjustable connection (5). There can be multiple secondary arms (6) as depicted in FIG. 1. The secondary arms may be short or long and, in some embodiments, their length is adjustable. The secondary arms (6) serve as a place to anchor the leg/foot restraints (7). The leg/foot restraints (7) attach to the person anywhere along the person's legs or feet. The leg/foot restraints (7) are constructed using any mechanism used to restrain a human appendage, including straps fastened by hook and loop fasteners, belts, cuffs, etc. The adjustable connections may be any kind of adjustable device that allows the distance between the secondary arms to be adjusted. For example, adjustable connections (2) and (5) may be constructed by having an internal gear (or gears) and ratchet, or they may be a slidable or rollable device. In a gear and ratchet system, a small movement of the primary arm (8) or the secondary arms (6) will cause the gear to advance to the next ratcheting position.

The main adjustable connection (2) provides many fixed positions of the primary arm (8). Some of these fixed positions lift the legs and buttocks of the person to a sufficient height for access to the buttocks for a diaper change. During a diaper change, a user may easily make adjustments to the height of the person's legs and buttocks off a surface on which the person is laying by moving the primary arm (8) in the direction of the desired adjustment.

In the embodiment in FIG. 1, the main adjustable connection has a locking mechanism, which may be any locking mechanism (i.e. friction, ratchet, etc.). In an alternative embodiment, the arms may be made of flexible gooseneck tubing or another material that resists movement. The term "locking mechanism" in this patent thus also includes the resistance to movement that flexible gooseneck tubing and other materials have in addition to more traditional locking mechanisms. The device would be considered "locked" when the person could not easily overcome the flexible gooseneck tubing's resistance to movement.

In some embodiments, a user must activate the release switch (3) to lock the primary arm (8) in a fixed position. In some embodiments, the locking mechanism may be set to lock in a designated position, and the user may adjust the designated position only when the release switch (3) is manually activated. In some embodiments, when the release switch (3) is released, the primary arm (8) automatically locks in the current position. In some embodiments, the locking mechanism may be set to allow the user to freely move the primary arm (8) upward without activating the release switch (3), but to prevent the user from moving the primary arm (8) downward unless the release switch (3) is activated. This embodiment allows the user to freely adjust the primary arm (8) upward to increase the height of the person's buttocks off the surface on which the person is laying without needing to manually actuate a releasing switch (3). In such a case, the primary arm (8) may be adjusted upward just by nudging the primary arm (8) with the back of the hand, wrist, or arm, which is especially helpful if the user's hands are soiled from the diaper change or if the user is holding something in his or her hand during the diaper change. In an alternative embodiment, activation of the release switch (3) would cause the height of the top of the primary arm (8) above the surface on which the person is laying to increase (or decrease) through electronic signaling and an internal motor.

One or more secondary adjustable connections (5) allow the user to adjust the separation of the person's legs. Separating the person's legs gives the caregiver improved access to the diaper area. The secondary adjustable connections (5) may be any kind of adjustable device that allows the distance between the secondary arms to be adjusted. For example, adjustable connections (5) may be constructed by having an internal gear (or gears) and ratchet, or they may be slidable or rollable devices.

The secondary adjustable connections (5) may have a locking mechanism, which may be any mechanism (i.e. friction, ratchet, etc.). The arms may also be made of flexible gooseneck tubing, which resists movement. The term "locking mechanism" in this patent thus also includes the resistance to movement that flexible gooseneck tubing has in addition to more traditional locking mechanisms. In some embodiments, a user must activate the release switch (4) to lock the second or third arms (6) in a fixed position. In some embodiments, the locking mechanism may be set to lock in a designated position, and the user may adjust the designated position only when the release switch (4) is manually activated. In some embodiments, when the release switch (4) is released, the second or third arm (6) automatically locks in the current position.

In some embodiments, the locking mechanism may be set to allow the user to freely move the first or second arm (6) outward without activating the release switch (4), but to prevent the user from moving the second or third arm (6) inward unless the release switch (4) is activated. This embodiment allows the user to freely adjust the second or third arm (6) outward to increase the separation of the person's legs without needing to manually actuate a release switch (4). In such a case, the second or third arm (6) may be adjusted outward just by nudging the second or third arm (6) with the back of the hand, wrist, or arm, which is especially helpful if the user's hands are soiled from the diaper change or if the user is holding something in his or her hand during the diaper change. In an alternative embodiment, activation of the release switch (4) would cause the distance between the secondary arms (6) to increase (or decrease) through electronic signaling and an internal motor.

The release switches (3) and (4) may be located in a variety of places on the device such as on the base (1), the primary arm (8) or the second or third arm (6). The release switches (3) and (4) can be designed to release any of the adjustable connections (2) and (5). The locking mechanisms and release switches (3) and (4) keep the device from being unlocked without user action when the person's buttocks have been lifted to an elevated state where the person would otherwise return to a prone position under his or her own weight.

Each device optionally has quick disconnects or hinges that allow the device to collapse and fold up into a smaller volume to allow for storage or travel. In some embodiments, the device folds flat to greatly lessen the space needed for storage or travel.

Figure 2:
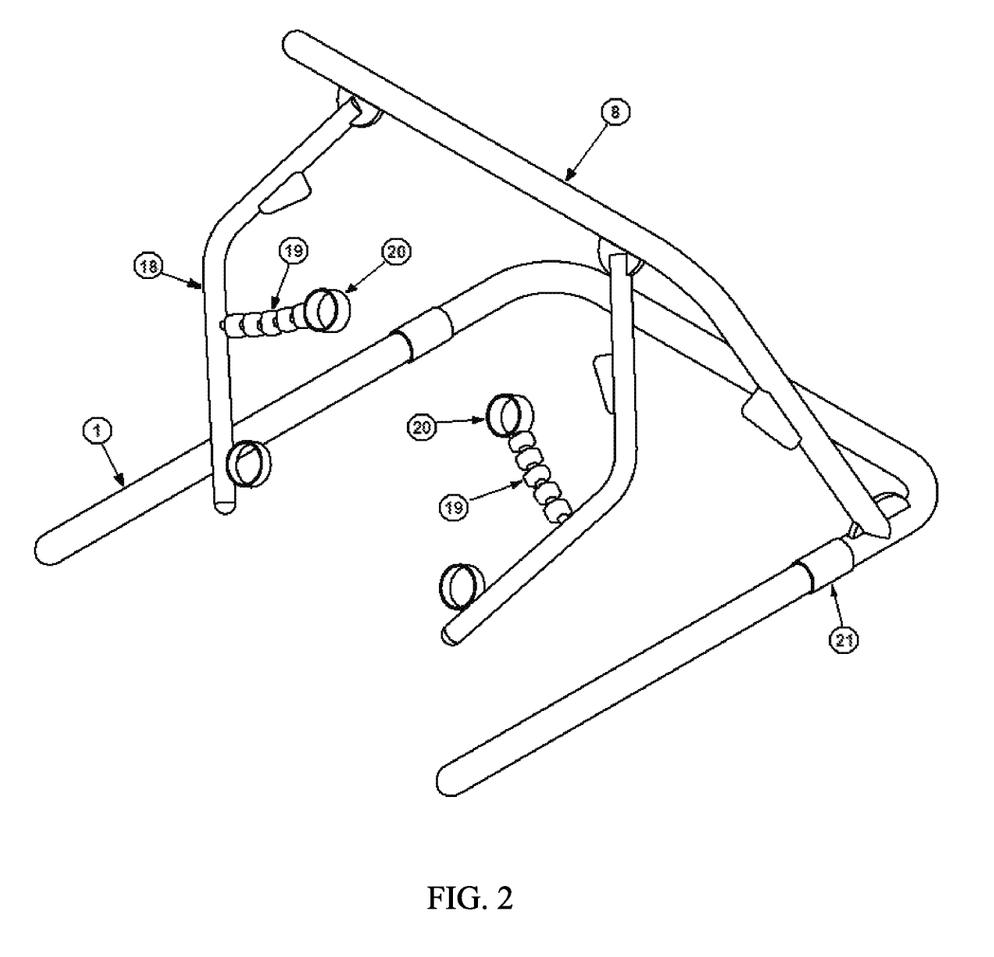
FIG. 2 is a perspective view of an alternative embodiment of the invention that includes curved arms and arm restraints.

Another embodiment of the invention is shown in FIG. 2. This embodiment has many of the same features as the embodiment in FIG. 1. However, unlike the secondary arms (6) in FIG. 1, the secondary arms (18) in FIG. 2 are curved to give the caregiver greater space to access the person. In addition, this embodiment includes arm restraints composed of a flexible segmented arm (19) connected to the secondary arms (18) with a restraining cuff (20) similar to that described in FIG. 1 (7). The flexible segmented arm (19) can be made with a variety of materials including a radius conveyor chain, side flexing modular (chain) belt, crate chain, multi flex chain, slat top chain, flat top chain, hinged slats, and connected slats. These restraints keep the person's arms away from the diaper area but give the person some freedom to move his arms for his comfort. Also illustrated is a separating segment (21) that allows the user to disassemble the unit for travel or storage.

Figure 3:
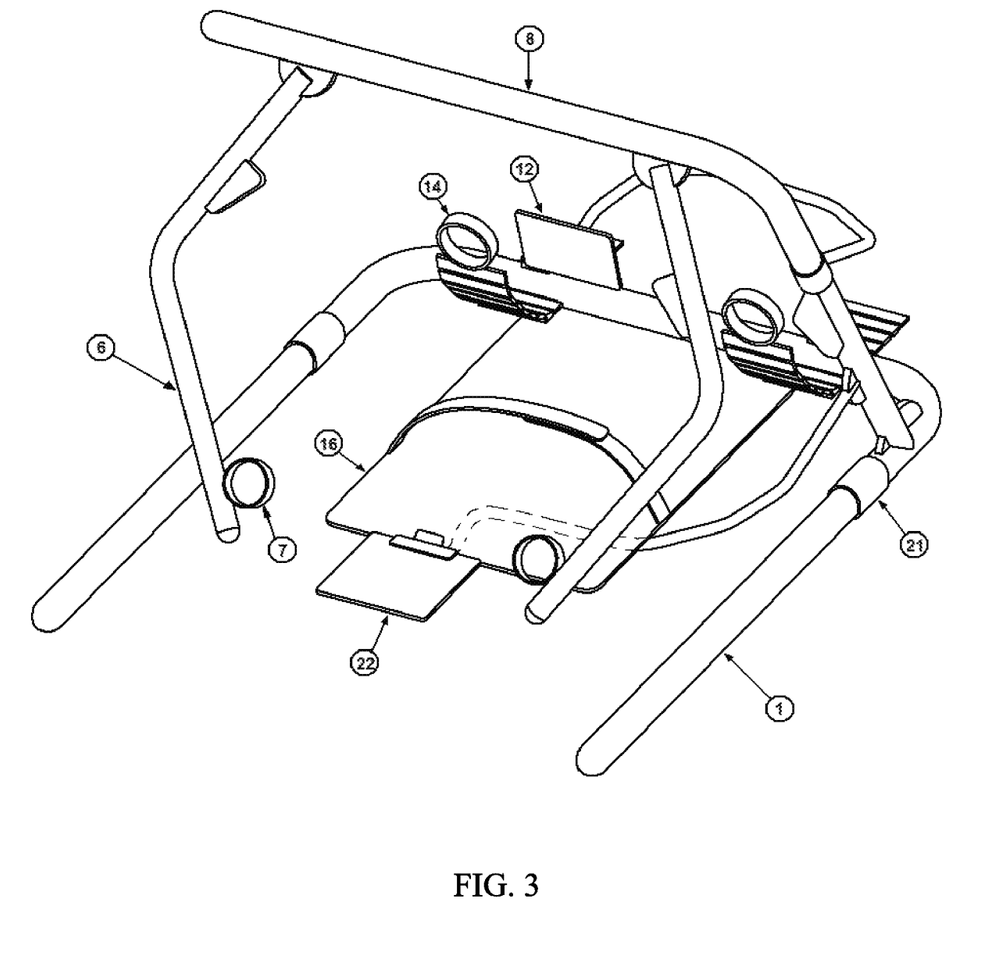
FIG. 3 is a perspective view of an alternative embodiment of the invention that includes curved arms, arm restraints, a chest or torso restraint, a flexible or semi-rigid pad, and absorbent pads connected to flexible or adjustable arms for catching waste.

Another embodiment of the present invention is shown in FIG. 3. This figure shows how multiple elements may come together and work in concert to enable the caretaker to more easily change a person's diaper. The embodiment in FIG. 3 includes curved secondary arms (6) to give the caregiver more space to access to the person's diaper area. This embodiment also includes a flexible or semi-rigid pad (16) upon which the person may be positioned and a chest or torso strap (17) to ensure that the person does not roll over. The semi-rigid pad (16) is capable of bending upward but has limited ability to bend side-to-side. One example of a semi-rigid pad is a bamboo mat or a mat resembling a bamboo mat but made out of plastic. Other examples include a radius conveyor chain, side flexing modular (chain) belt, crate chain, multi flex chain, slat top chain, flat top chain, hinged slats, and connected slats.

The embodiment in FIG. 3 includes arm restraints (14) to keep the person's hands away from the diaper area. This embodiment includes a system for absorbing urine with one or more absorbent pads mounted on bases (12) or (22). The absorbent pad may be a diaper, which can be used on the person if the person does not soil that diaper during the diaper change. This embodiment also includes separating points (21) allowing the unit to be disassembled for travel or storage. Alternatively, the entire device can collapse for easy travel or storage.

Figure 4:
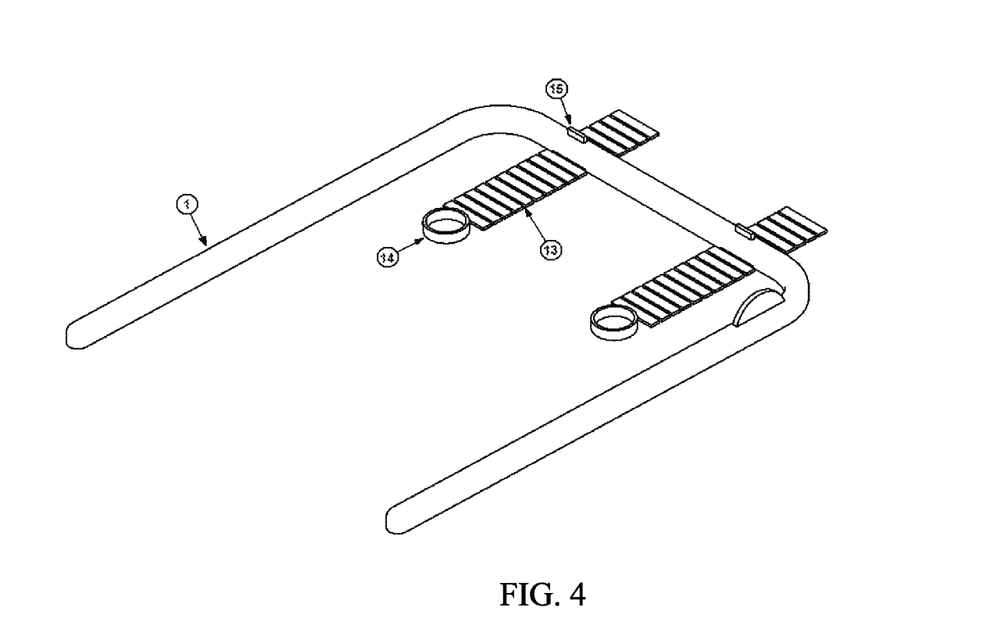
FIG. 4 is a perspective view of an example of arm restraints connected to a base. In this example, the arm restraints are connected to a tubular base.
Figure 5:
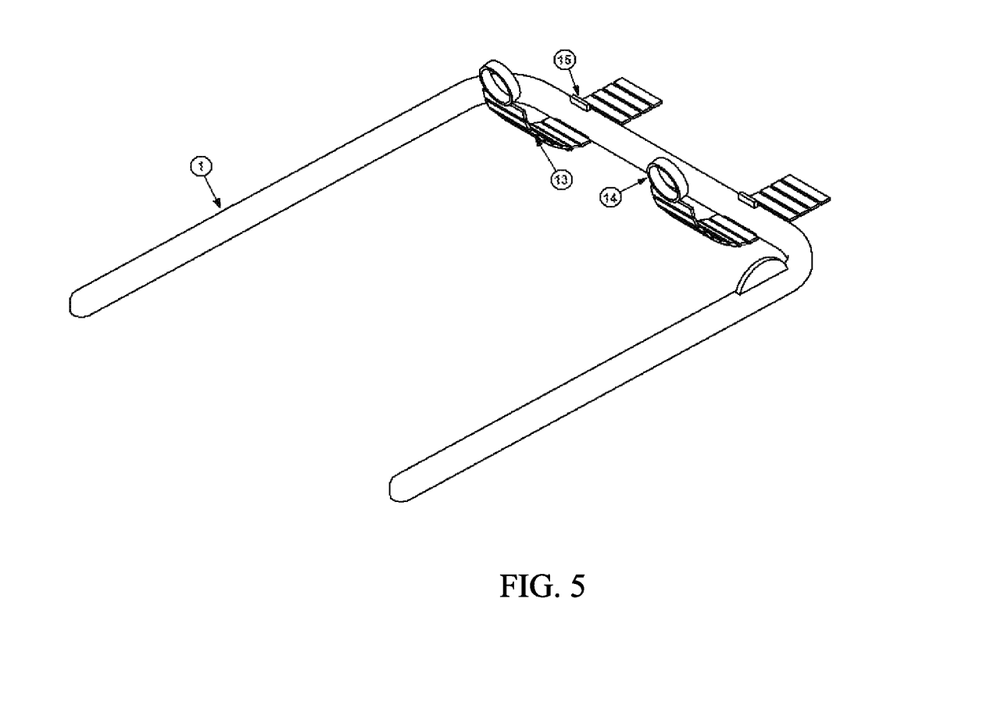
FIG. 5 is a perspective view showing an example of how the arm restraints of FIG. 4 may bend to allow for the person to have some movement of his hands.

The arm restraints are illustrated in FIGS. 4 and 5. Although the primary arm (8), the secondary arms (6) and the leg/foot restraints (7) in FIG. 1 could also be present, they are omitted from this figure for clarity. These restraints allow the person limited use of his or her arms so as to give some comfort to the person while preventing the person from interfering with diapering activities. The arm restraints also give the caretaker enough flexibility to adjust the person's position to clean the diaper areas.

The arm restraints may be secured to any part of the device, such as the base (1) or the second or third arms (6) in FIG. 1. In FIGS. 4 and 5, the arm restraints are secured to the base (1). In some embodiment, the length of the strap (13) may be adjusted by activating an adjustor (15) and sliding the strap through the base to make it longer or shorter and then locking it back into place with the adjustor (15). The limited flexibility of the strap (13) is intended to not only help restrain the person, but to reduce the possibility of the strap from becoming entangled. The straps (13) may be made from a variety of materials, including a common metal wristwatch strap, plastic, or fabric. The arm restraints may also be constructed with a flexible segmented arm like (19) in FIG. 1. The arm restraints can be made with a variety of materials including a radius conveyor chain, side flexing modular (chain) belt, crate chain, multi flex chain, slat top chain, flat top chain, hinged slats, and connected slats. FIG. 4 shows the flexibility of the arm restraints (13) and (14) as they are bending upward.

Figure 6:
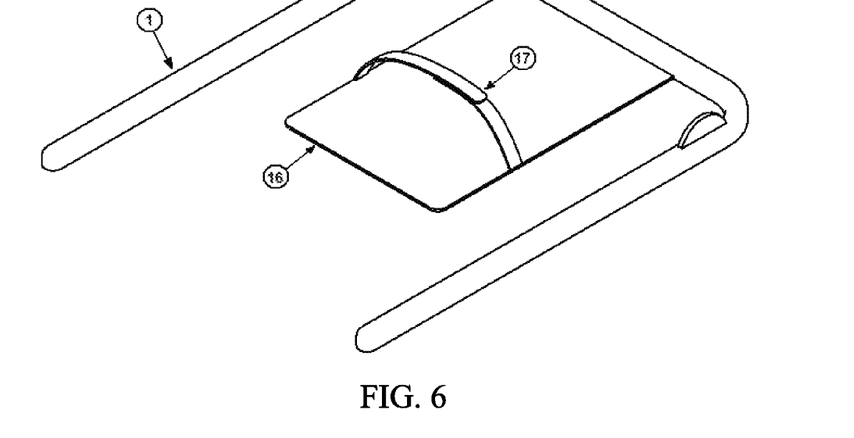
FIG. 6 is a perspective view of the chest or torso restraint and a flexible or semi-rigid pad designed to prevent the person from rolling over. In this example, the flexible or semi-rigid pad is connected to a tubular base.
Figure 7:
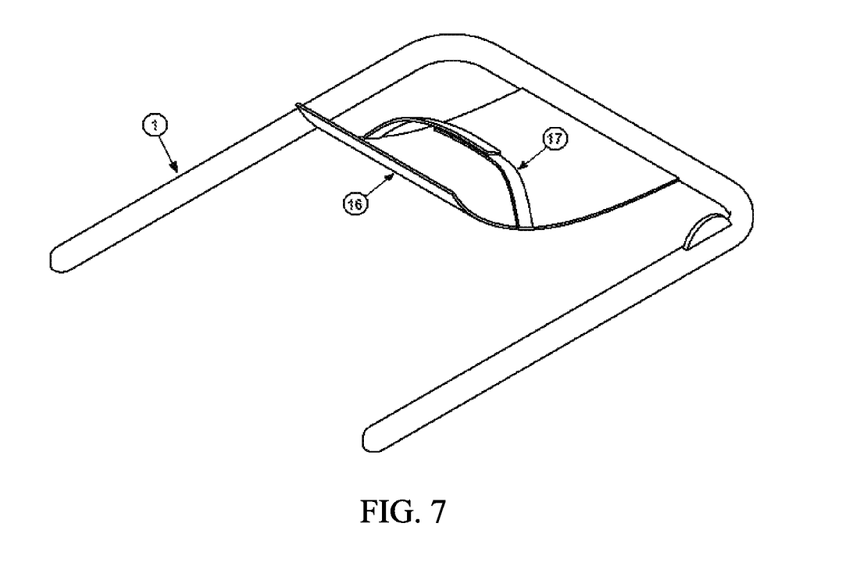
FIG. 7 is a perspective view showing how the flexible or semi-rigid pad of FIG. 6 may curve upward to allow some movement so a caregiver may lift the person's buttocks during a diaper change. The flexible or semi-rigid pad has limited ability to twist side-to-side to restrain the person enough to prevent him from rolling over.

FIGS. 6 and 7 illustrate an embodiment with a flexible or semi-rigid pad (16) and a chest or torso strap (17). The flexible or semi-rigid pad (16) may be attached to the base (1) and optionally another surface such as the wall, furniture, or the surface on which the flexible or semi-rigid pad rests. The flexible or semi-rigid pad (16) and the base (1) may be one unified piece or they may be separate pieces that have been connected to each other. In FIG. 6, the base (1) is elongated, but the shape of the base may be any shape that supports the apparatus. The chest or torso strap (17), which is connected to the flexible or semi-rigid pad (16), is designed to prevent the person from rolling over or otherwise moving too much that the caregiver's ability to change a diaper is inhibited. A hook and loop fastener or any other similar fastener may be used to close the chest strap (17) over the person. FIG. 7 shows how the flexible or semi-rigid pad (16) may curl upward so that it can raise or lower along with the raising or lowering of the person's buttocks. The flexible or semi-rigid pad (16) is designed to have limited mobility in the side-to-side direction to prevent the person from rolling over. One example of a semi-rigid pad is a bamboo mat or a mat resembling a bamboo mat but made out of plastic. Other examples include a radius conveyor chain, side flexing modular (chain) belt, crate chain, multi flex chain, slat top chain, flat top chain, hinged slats, and connected slats. In one embodiment, the flexible or semi-rigid pad (16) is flexible in the direction illustrated in FIG. 7 to allow a caregiver to lift, move, and turn a person, but has limited flexibility in other directions (such as twisting side-to-side). Although the primary arm (8), the secondary arms (6) and the restraints (7) in FIG. 1 could also be present, they are omitted from FIG. 6 for clarity.

Figure 11:
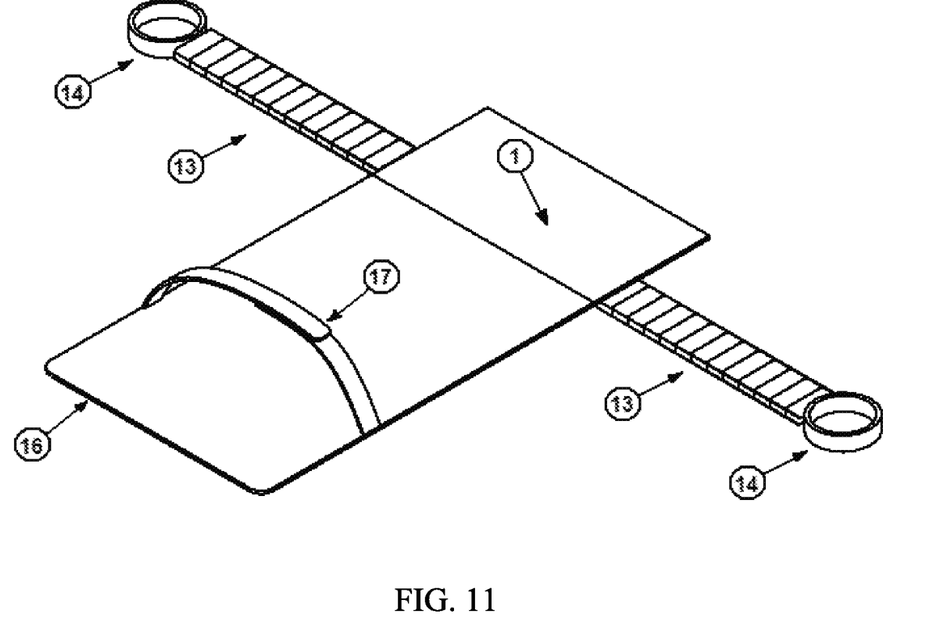
FIG. 11 is a perspective view of an alternative embodiment of the invention that includes arm restraints, a chest or torso restraint, and a flexible or semi-rigid pad designed to prevent the person from rolling over. In this embodiment, the flexible or semi-rigid pad is connected to a flat base.

FIG. 11 illustrates a similar embodiment to the embodiment shown in FIG. 6. In FIG. 11, the flexible or semi-rigid pad (16) is connected to a flat base (1) rather than the elongated base in FIG. 6. The flexible or semi-rigid pad (16) and the flat base (1) may be one unified piece or they may be separate pieces that have been connected to each other.

Figure 8:
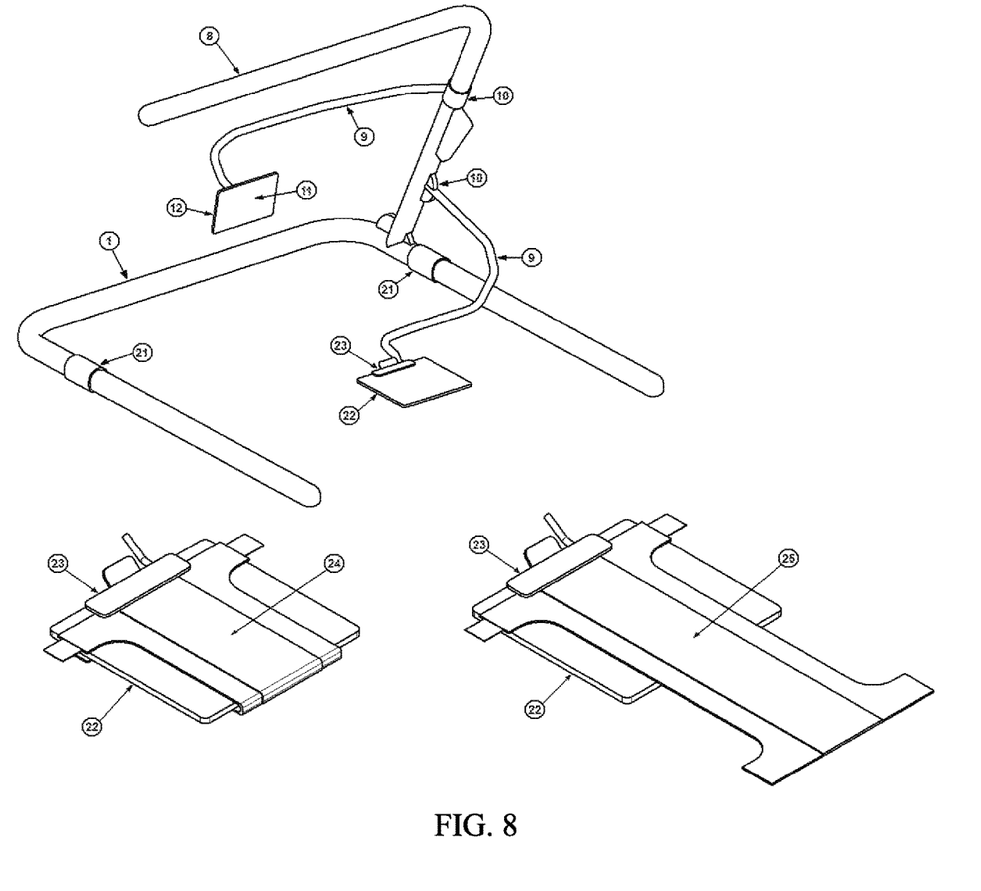
FIG. 8 is a perspective view of absorbent pads for collecting urine connected to flexible or adjustable arms.

FIG. 8 illustrates an embodiment with absorbent pads (24) and (25) fastened to a base (22) and connected to the device via flexible or adjustable arms (9). Frequently during a diaper change, a person will urinate and soil the person's clothing and the surface on which the person is lying. The absorbent pads (24) and (25) and arms (9) help contain any additional waste that a person produces during a diaper change. The absorbent pads (24) and (25) may be adjusted to catch this waste and prevent it from soiling the person or the caregiver (or others in the vicinity) during a diaper change. The absorbent pads (24) and (25) may be a diaper, which can be used on the person if it is not soiled during the diaper change.

The absorbent pads (24) and (25) may be positioned on the top of the penis or directly in the projected path of a stream of urine. This location would prevent a male person from urinating on himself, the caretaker, and the surroundings. The absorbent pads (24) and (25) may be positioned on the extreme lower back and top of the buttocks. Placing absorbent pads (24) and (25) at this position could prevent the person from soiling the surface on which he is lying as well as preventing other spontaneous waste from reaching undesirable locations.

Two embodiments for the absorbent pad system are specifically illustrated. The first embodiment uses disposable or washable, removable absorbent pads (11) on base (12). This embodiment may employ a fastening system such as a clip, hook and loop, or snap etc. to join the base (12) to the absorbent pad (11). The absorbent pad itself may be constructed of any material that is suitable for absorbing or containing waste, such as cloth or synthetic materials with or without an additional absorbent core. The second embodiment has a base (22) designed to receive a diaper or absorbent pad (24). The diaper or absorbent pad (24) will serve the purpose of catching stray waste. This embodiment can double as a staging system for a new diaper (25).

In the above embodiments, the absorbent pad (11) or diaper or absorbent pad (24) may be attached to the bases (12) and (22), respectively, which are attached to the adjustable arms (9). The adjustable arms (9) can be rigid and attached by a rotating joint (10) to allow the pad to be positioned anywhere convenient. The adjustable arms (9)

may also be flexible but with enough resistance to prevent the person from altering their position. The rotating joint (10) may have a built in tensioning device such as a spring to cause the device to tend toward a preferred location. This would allow the absorbent pad (11) or diaper (24) to stay in contact with the person, even if the person moves positions. The absorbent pad (11) may also be constructed of a springy material such as a sponge to help the pad maintain contact with the person's body if he changes positions.

In FIG. 8, the base (22) provides a structure that the diaper can be wrapped around securely (24) by a clip (23) or other fastening mechanism. Also, the diaper may be open and partially freed (25), allowing the diaper to be wrapped around the person for diapering. Although the secondary arms (6) and restraints (7) in FIG. 1 could also be present, they are omitted from this figure for clarity.

Figure 9:
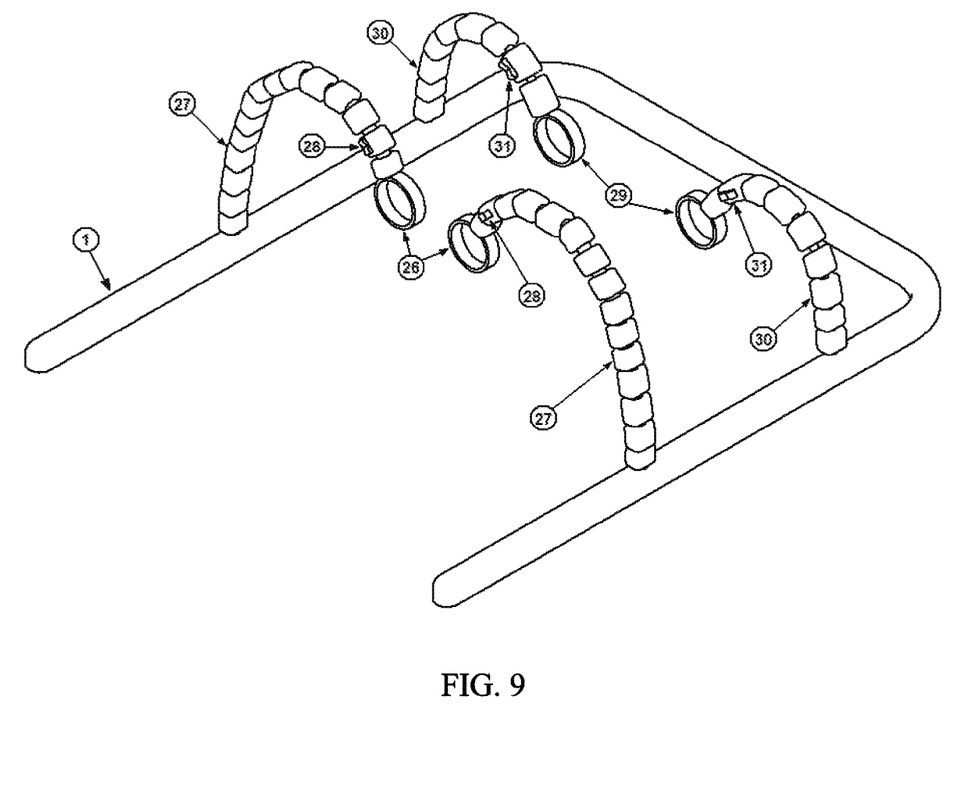
FIG. 9 is a perspective view of an alternative embodiment of the invention wherein both the leg restraints and arm restraints are attached to locking, segmented arms or flexible gooseneck tubing. The flexible gooseneck tubing has resistance to movement that an infant or person cannot easily overcome. The term "locking mechanism" in this patent includes the resistance to movement that flexible gooseneck tubing and other materials exhibit in addition to more traditional locking mechanisms.

Another embodiment of the invention is shown in FIG. 9. In this embodiment, both the leg/foot restraints (26) and the arm restraints (29) are attached to locking, segmented arms (27) and (30), respectively. The segmented arms (27) and (30) are attached to the base (1). This embodiment includes controls (28) and (31) for locking the segmented arms (27) and (30) in fixed positions. These controls (28) and (31) may be located on the segmented arms (27) and (30) in such a way to maximize the caretaker's ability to activate the controls and adjust the arm simultaneously, and with one hand if necessary. The restraints (26) and (29) may be like those described in FIG. 1 (7).

Alternatively, the arms (27) and (30) may be flexible or adjustable arms, segmented or otherwise, which resist movement like flexible gooseneck tubing. The resistance would aid in restraining the person without preventing the caretaker from manipulating the arms. In such embodiments, a locking control (28) and (31) could be present or the resistance to movement can serve as the locking mechanism. Or, the arms could "lock" when they resist movement enough to prevent the person from overcoming the resistance to movement. The term "locking mechanism" in this patent includes the resistance to movement that flexible gooseneck tubing has in addition to more traditional locking mechanisms. In the embodiment with arms made of flexible gooseneck tubing or locking, segmented arms or other adjustable materials, an adjustable connection to the base is optional because the materials of the arms provide the adjustment irrespective of whether there is an adjustable connection to the base.

Figure 10:
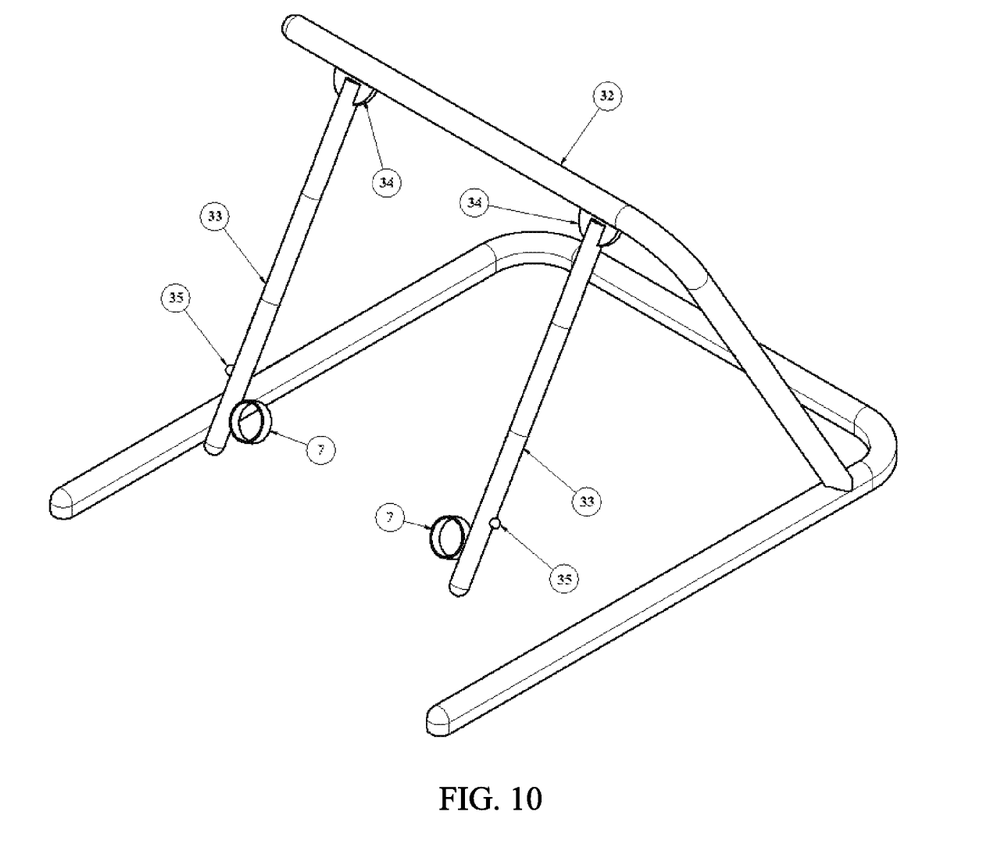
FIG. 10 is a perspective view of an alternative embodiment of the invention wherein the primary arm is fixed in place relative to the base and the secondary arms are extendable to allow for adjusting the length of the secondary arms.

FIG. 10 illustrates an embodiment of the invention wherein the secondary arms (33) are extendable and attached via an adjustable connection (34) to the primary arm (32). The adjustable connection (34) may be any kind of adjustable device that allows the distance between the secondary arms to be adjusted. For example, adjustable connection (34) may be constructed by having an internal gear (or gears) and ratchet, or it may be a slidable or rollable device. The secondary arms are extendable to allow for adjusting the length of the secondary arms. The extendable nature of the secondary arms (33) may either be from the adjustable connection (34) also allowing the arms to move along the direction of their length or from the secondary arms (33) being, themselves, telescopic or extendable. The primary arm (32) is in a fixed position relative to the base. The restraints (7) are attached to the secondary arms (33). This embodiment allows for the height of the person's legs and buttocks to be adjusted before, during, or after a diaper change by activating release switch (35) and moving the secondary arms (33) upward or downward. The distance between the secondary arms (33) may also be adjusted before, during, or after a diaper change due to the adjustable connection (34).

One of ordinary skill in the art will readily understand that the invention described herein may be practiced using different combinations of the disclosed features. In addition, although a number of preferred embodiments have been shown and described, it would be apparent to one of ordinary skill in the art that certain modifications, variations, and alternatives may be made while remaining within the spirit and scope of the invention.

What is claimed is:

1. A diaper changing apparatus comprising:
   (a) a base;
   (b) a primary arm extending from the base;
   (c) a first secondary arm and a second secondary arm extending from the primary arm via a first adjustable connection and second adjustable connection;
   wherein the orientation of the first and second secondary arms is adjustable via at least one of the first adjustable connection or the second adjustable connection;
   (d) a first restraining member and a second restraining member adapted for restraining appendages of the person, said first restraining member and said second restraining member are connected to the first and second secondary arms; and
   whereby increasing the distance between the first restraining member and a surface on which a person is lying and the second restraining member and the surface on which the person is lying lifts the buttocks of the person upward from the surface on which the person is lying, and wherein the first secondary arm and the second secondary arm are configured to adjust the distance between the first restraining member and the second restraining member and separate the person's appendages via the first adjustable connection and the second adjustable connection.

2. The diaper changing apparatus of claim 1 wherein the secondary arms are extendable allowing for adjustments to the length of the secondary arms.

3. The diaper changing apparatus of claim 1 further comprising a fastening mechanism that operates to fasten the base to the surface.

4. The diaper changing apparatus of claim 1 further comprising an absorbent pad connected to a tertiary arm, said tertiary arm connected to either the base, primary arm, or secondary arms, the absorbent pad capable of absorbing urine.

5. The diaper changing apparatus of claim 1 further comprising a semi-rigid pad connected to the base, and a restraint strap connected to said semi-rigid pad that is adapted to be positioned across the chest or torso of the person, said semi-rigid pad capable of bending up and down as a caregiver lifts the person's buttocks during a diaper change but with limited capability of twisting side-to-side so as to impede the person's ability to roll over.

6. The diaper changing apparatus of claim 1 further comprising a pair of arm restraints connected to the base, said pair of arm restraints adapted for restraining the person's hands or arms and preventing the person's hands from accessing the pelvic region.

7. The diaper changing apparatus of claim 1, wherein the distance between the top of the primary arm and the surface on which the person is lying is adjustable via a third adjustable connection attaching the base to the primary arm.

8. The diaper changing apparatus of claim 1, wherein the first secondary arm and the second secondary arm are connected by the primary arm.

9. The diaper changing apparatus of claim 1, further comprising a locking mechanism adapted to allow for fixing the position of the primary arm in place or releasing it for further adjustment.

10. The diaper changing apparatus of claim 1, further comprising a second locking mechanism adapted to allow for fixing the position of the first and second secondary arms in a particular orientation or releasing them for further adjustment.

11. A diaper changing apparatus comprising:
(a) a base;
(b) a primary arm extending only from a longitudinal side of the base;
(c) a first secondary arm and a second secondary arm extending from the primary arm;
(d) a first adjustable connection attaching the first and second secondary arms to the primary arm; wherein the orientation of the first and second secondary arms is adjustable via the first adjustable connection;
(g) a first restraining member and a second restraining member adapted for restraining appendages of a person, said first restraining member and said second restraining member connected to the first and second secondary arms;
whereby increasing the distance between the first restraining member and a surface on which the person is lying and the second restraining member and the surface on which the person is lying lifts the buttocks of the person upward from the surface on which the person is lying, and whereby increasing the distance between the first restraining member and the second restraining member separates the person's appendages.

12. The diaper changing apparatus of claim 11, wherein the distance between the top of the primary arm and the surface on which the person is lying is adjustable via a third adjustable connection attaching the base to the primary arm.

13. The diaper changing apparatus of claim 11, wherein the first secondary arm and the second secondary arm are connected by the primary arm.

14. The diaper changing apparatus of claim 11, further comprising a locking mechanism adapted to allow for fixing the position of the primary arm in place or releasing it for further adjustment.

15. The diaper changing apparatus of claim 11, further comprising a second locking mechanism adapted to allow for fixing the position of the first and second secondary arms in a particular orientation or releasing them for further adjustment.

16. A diaper changing apparatus comprising:
(a) a base;
(b) a primary arm extending only from a longitudinal side of the base;
(d) a first restraining member adapted for restraining an appendage of a person, said first restraining member is connected to the primary arm via a first adjustable connection;
(e) a second restraining member adapted for restraining another appendage of a person, said second restraining member is connected to the primary arm via a second adjustable connection; wherein the distance between the first restraining member and the second restraining member is adjustable via the first adjustable connection or second adjustable connection; and
wherein the first and second restraining members are configured to suspend the person's appendages from the primary arm.

17. The diaper changing apparatus of claim 16, wherein the distance between the top of the primary arm and the surface on which the person is lying is adjustable via a third adjustable connection attaching the base to the primary arm.

18. The diaper changing apparatus of claim 16, further comprising a locking mechanism adapted to allow for fixing the position of the primary arm in place or releasing it for further adjustment.

19. A diaper changing apparatus comprising:
(a) a base;
(b) a plurality of primary arms extending from the base;
(e) a first restraining member adapted for restraining an appendage of a person, said first restraining member connected to at least one of the primary arms via a first adjustable connection;
(f) a second restraining member adapted for restraining another appendage of a person, said second restraining member connected to at least one of the primary arms via a second adjustable connection; wherein the distance between the first restraining member and the second restraining member is adjustable via the first adjustable connection or second adjustable connection;
wherein the first and second restraining members are configured to extend from at least one of the primary arms toward the base without touching the base; and
wherein the first restraining member is configured to suspend the appendage of the person from at least one of the primary arms and the second restraining member is configured to suspend another appendage of the person from at least one of the primary arms.

20. The diaper changing apparatus of claim 19, wherein the distance between the top of each of the primary arms and the surface is adjustable.

21. The diaper changing apparatus of claim 19, further comprising a third adjustable connection attaching each of the primary arms to the base.

* * * * *